United States Patent
Wan et al.

(10) Patent No.: US 6,177,548 B1
(45) Date of Patent: Jan. 23, 2001

(54) ENHANCED AGGREGATE REMOVAL FROM BULK BIOLOGICALS USING ION EXCHANGE CHROMATOGRAPHY

(75) Inventors: Min Wan, Cary, NC (US); George Y. Wang, Houston, TX (US)

(73) Assignee: Tanox, Inc., Houston, TX (US)

( * ) Notice: Under 35 U.S.C. 154(b), the term of this patent shall be extended for 0 days.

(21) Appl. No.: 09/170,411

(22) Filed: Oct. 13, 1998

Related U.S. Application Data

(60) Provisional application No. 60/061,842, filed on Oct. 14, 1997.

(51) Int. Cl.[7] ...................................................... C07K 16/00
(52) U.S. Cl. ...................................... 530/390.5; 530/390.1
(58) Field of Search ............................... 530/387.1, 388.1, 530/390.1, 390.5

(56) References Cited

U.S. PATENT DOCUMENTS 5,110,913 * 5/1992 Coan et al. ........................ 530/388

\* cited by examiner

*Primary Examiner*—Donna C. Wortman
*Assistant Examiner*—Robert A. Zeman
(74) *Attorney, Agent, or Firm*—Eric P. Mirabel

(57) ABSTRACT

Disclosed are methods and processes for removing aggregates and other impurities from partially purified protein bulk product, in particular, from partially purified monoclonal antibody, using anion exchange chromatography. In such methods and processes, the pH of the sample is adjusted to be lower than the isoelectric point of the product, preferably by 0.2 logs, and the sample is passed through an ion exchange matrix which is equilibrated to bind the aggregates and host cell DNA as well as endotoxins in the sample.

5 Claims, No Drawings

ENHANCED AGGREGATE REMOVAL FROM BULK BIOLOGICALS USING ION EXCHANGE CHROMATOGRAPHY

This application claims the benefit of U.S. provisional application Ser. No. 60/061,842 filed Oct. 14, 1997, the content of which is incorporated herein by reference.

FIELD OF THE INVENTION

The invention relates to removal of proteinaceous aggregates from bulk biologicals, especially pharmaceutical biologicals, using ion exchange chromatography.

BACKGROUND OF THE INVENTION

In the manufacturing of biopharmaceuticals using cell culture processes, one problem has been that proteins in the cell culture can form aggregates. The aggregates are usually formed by more than one molecule, or contain partially or completely denatured molecules. Aggregates are not usually removed in filtering or other preliminary purification processes because of their similarity to the biopharmaceutical product.

Aggregates can be a problem in biopharmaceutical manufacture. The aggregate level of the starting bulk must be kept below 0.1% in order to formulate high strength biopharmaceutical products, i.e., greater than 100 mg/ml, with an acceptably low aggregate concentration. Therefore, elimination of aggregates from the bulk product in an efficient manner is needed for successful production of high strength biopharmaceuticals.

A conventional method to remove aggregates from biological solution is by gel filtration, which is based on the molecular size difference between aggregates and product molecules. However, this method is difficult and costly for large scale production and when one wishes to concurrently remove other impurities, including endotoxins and nucleic acids, for production of high strength pharmaceuticals.

SUMMARY OF THE INVENTION

The invention includes methods and processes for removing aggregates from partially purified bulk product, in particular, from partially purified monoclonal antibody, using anion exchange chromatography. The invention is based on the principle that, because aggregates are larger and have a different conformation than biological product molecules, aggregates carry more charges near to the cell culture product's isoelectric point than do the products themselves.

When the working pH is close to the product's isoelectric point, the charge on the product molecules is low. Aggregates generally carry more charge(s) than the product at this pH range, because of the components and the conformation of the aggregates. Thus, when the pH is adjusted to near the isoelectric point of the products and the sample is loaded on an ion exchange column, more of the charged aggregates than product will be bound on the column, resulting in a greater degree of aggregate removal than using other chromatographic conditions.

Preferably, the pH of the loading sample would be adjusted to 0.2 logs lower than the pI of the product to achieve aggregate removal. Also, passing the partially purified product through the anion exchange matrix accomplishes removal of other impurities, including host cell DNA and endotoxins.

Making and Using the Invention

The methods and processes of the invention can be used in purification of any type of biopharmaceutical in a cell culture process, where one wishes to remove aggregates and other impurities, including nucleic acids and endotoxins, in a simple and efficient manner. It can be used in either small scale or large scale production, but it leads to greater increases in efficiency and greater cost savings in large scale production. These methods and processes are effective in purification in both mammalian and bacterial cell culture processes. Because mammalian cell culture is often larger scale than bacterial cell culture, however, it would be expected to be used more often in mammalian cell culture processes.

Antibody production frequently involves production of large quantities of product, and therefore, production on a large scale. It is, therefore, particularly well-suited for purification through the methods and processes of the invention. Examples of using the methods of the invention to remove aggregates from a production bulk for a humanized antibody (Hu-901) follows.

EXAMPLE 1

Purification and Aggregate Removal of a Monoclonal Antibody from Cell Broth (Small Scale)

Harvested conditioned medium containing unpurified Hu-901 (a humanized monoclonal antibody) is passed through an immobilized protein A column (IPA, BioProcessing, Princeton, N.J.). The bound fraction is eluted and neutralized. This fraction is adjusted with a suitable salt solution and applied to a hydrophobic interaction column (HIC, Pharmacia Biotech, Picataway, N.J.). The intact antibody fraction binds to the column and is eluted by a low salt strength buffer. This fraction is then buffer exchanged to the desired buffer condition using either a Stirred Cell (Amico, Beverly, Mass.), for small scale experiments, or a tangential flow filtration (TFF) device (Pall Filtron, Northborough, Mass.), for large scale production. The buffer exchanged antibody fraction is used as set forth below.

A Q Sepharose FF (Pharmacia Biotech, Picataway, N.J.), 5.1(H)×1 (D) cm, column volume (CV): 4.01 ml, column is flushed with 5 CV of water for injection (WFI) at a flow rate of 3.93 ml/min (300 cm/hr) before starting. The column is then conditioned with 5 CV of sodium chloride (1 M), and pre-equilibrated with 5 CV of potassium phosphate buffer (0.2 M, pH 8.0). Before loading, the column is equilibrated with 5 CV of potassium phosphate buffer (10 mM, pH 8.2). The isoelectric point of the Hu-901 antibody is in the pH range of 8.1 to 8.7. 8 ml of a sample of the buffer exchanged antibody (in 10 mM potassium phosphate buffer, pH 8.2) is loaded onto the column at a flow rate of 1.96 ml/min (150 cm/hr). The passed through fraction is collected as soon as the absorbance on the UV detector (280 nm) starts to increase. The column is washed with 10 CV of potassium phosphate buffer (10 mM, pH 8.2). The collection of the passing through fraction is stopped when the UV absorbance is less than 10% of the peak height. The bound protein on the column is eluted with 5 CV of sodium chloride (1 M) at a flow rate of 3.93 ml/min (300 cm/hr). The column is regenerated with 5 CV of cleaning solution (1 M sodium hydroxide/1 M sodium chloride) and stored in 0.01 M sodium hydroxide solution. A table of the results follows.

TABLE I

| | |
|---|---|
| Load sample volume: | 8 ml |
| Loading Ab concentration: | 12.14 mg/ml |
| Total Ab by loading: | 97.12 mg |
| Volume of collected fraction: | 47 ml |
| Ab concentration in collection fraction: | 1.924 mg/ml |
| Total Ab in collected fraction: | 90.48 mg |
| Ab recovered in collected fraction: | 93.11% |
| Aggregation level in loading sample: | 0.55% |
| Total aggregates in loading sample: | 0.534 mg |
| Aggregation level in collected fraction: | 0.14% |
| Total aggregates in collected fraction: | 0.126 mg |
| Total aggregates removed: | 0.408 mg |
| Aggregates removal: | 76.4% |
| Column capacity for aggregates: | 0.102 mg/ml resin |

EXAMPLE 2

Removing Aggregates: Production Scale

An experiment to determine if the methods of the invention were useful for purifying and removing aggregates from a partially purified product bulk on a production scale were carried out under the following conditions.

A Q Sepharose FF, 24 (H)×20 (D) cm, column volume (CV): 7.54 L, was used. The sample to be purified was 13–16 L partially purified Hu-901 in 10 mM Potassium Phosphate buffer, pH 8.03, 10–12 g Ab/L, aggregation level: 0.4–0.5%; total aggregates: 0.5–0.9 g for each batch. The flow rate used in the experiment was 680 ml/min (130 cm/hr) for loading and washing and 900 ml/min (172 cm/hr) for all the other steps. The procedures used in this experiment are summarized below in Table II.

TABLE II

| | | Volume | | Flow Rate | | Time |
|---|---|---|---|---|---|---|
| Step | Solution | CV | L | cm/hr | ml/min | min |
| Flush | WFI | 4 | 30.6 | 172 | 900 | 34 |
| Regeneration | 1M NaCl/1M NaOH | 4 | 30.6 | 172 | 900 | 34 |
| Flush | WFI | 4 | 30.6 | 172 | 900 | 34 |
| Condition | 1M NaCl | 4 | 30.6 | 172 | 900 | 34 |
| Pre-equilibration | 0.2M Potassium Phosphate buffer, pH 8.0 | 5 | 37.8 | 172 | 900 | 42 |
| Equilibration | 10 mM KPi, pH 8.03 | 7 | 53.1 | 172 | 900 | 59 |
| Loading | Sample | 2.06 | 15.51 | 130 | 680 | 22.8 |
| Wash | 10 mM KPi, pH 8.03 | 8.03 | 60.5 | 130 | 680 | 89 |
| Strip | 1M NaCl | 4 | 30.6 | 172 | 900 | 34 |
| Flush | WFI | 4 | 30.6 | 172 | 900 | 34 |
| Regeneration | 1M NaCl/1M NaOH | 4 | 30.6 | 172 | 900 | 34 |
| Flush | WFI | 4 | 30.6 | 172 | 900 | 34 |
| Store | 0.01M NaOH | 4 | 30.6 | 172 | 900 | 34 |

The results of these experiments are summarized below in Table III.

TABLE III

| | Run 1 | Run 2 | Run 3 |
|---|---|---|---|
| Load sample volume: | 13.78 L | 13.40 L | 15.51 L |
| Loading Ab concentration: | 10.50 g/L | 10.49 g/L | 11.85 g/L |
| Total Ab by loading: | 144.69 g | 140.57 g | 183.79 g |
| Volume of collected fraction: | 53.25 L | 55.20 L | 55.02 L |
| Ab concentration in collected fraction: | 2.55 g/L | 2.49 g/L | 3.21 g/L |
| Total Ab in collected fraction: | 135.96 g | 137.43 g | 176.61 g |
| Antibody recovered in collected fraction: | 93.97% | 97.77% | 96.09% |
| Aggregation level in loading sample: | 0.4% | 0.4% | 0.45% |
| Total aggregates in loading sample: | 0.579 g | 0.562 g | 0.827 g |
| Aggregation level in collected fraction: | 0.1% | 0.03% | 0.1% |
| Total aggregates in collected fraction: | 0.136 g | 0.041 g | 0.177 g |
| Total aggregates removed: | 0.443 g | 0.519 g | 0.650 g |
| % aggregate removed: | 76.5% | 92.3% | 78.6% |
| Column capacity for aggregates | 0.059 g/L resin | 0.069 g/L resin | 0.086 g/L resin |

These results collectively show that the aggregated monoclonal antibody could be effectively removed by Q Sepharose Fast Flow anion exchanger chromatography after adjusting the sample's buffer pH to near its isoelectric point. The recovery in this experiment was 93–98%, while the efficiency of aggregate removal is over 75%.

It should be understood that the terms and expressions and examples used above are exemplary only and not limiting, and that the scope of the invention is defined only in the claims which follow, and includes all equivalents of the subject matter of those claims.

What is claimed is:

1. A method of removing aggregates and other impurities from a biological sample, comprising:

adjusting the pH of the sample to 0.2 logs lower than the isoelectric point of the biological sample;

passing the biological sample through a means for ion exchange which is charged so as to bind the aggregates in the biological sample.

2. The method of claim 1 wherein the means for ion exchange is an anion exchanger matrix.

3. The method of claim 1 wherein the biological sample includes a biopharmaceutical product.

4. The method of claim 3 wherein the biopharmaceutical product is a monoclonal antibody.

5. The method of claim 1 wherein impurities are removed by the means for ion exchange.

* * * * *